US007655254B2

(12) United States Patent
Dennis et al.

(10) Patent No.: US 7,655,254 B2
(45) Date of Patent: Feb. 2, 2010

(54) IMPLANTABLE DEVICE FOR CONTINUOUS DELIVERY OF INTERFERON

(75) Inventors: Paula Dennis, Auburn, CA (US); Michael A. Desjardin, Sunnyvale, CA (US); Stan Lam, Dublin, CA (US); Kui Liu, Redwood City, CA (US); James E. Matsuura, Fort Collins, CO (US); Latha Narayanan, San Francisco, CA (US); Catherine M. Rohloff, Los Altos, CA (US); Pauline C. Zamora, Sausalito, CA (US)

(73) Assignee: Intarcia Therapeutics, Inc., Hayward, CA (US)

( * ) Notice: Subject to any disclaimer, the term of this patent is extended or adjusted under 35 U.S.C. 154(b) by 0 days.

(21) Appl. No.: 11/347,601

(22) Filed: Feb. 3, 2006
(Under 37 CFR 1.47)

(65) Prior Publication Data

US 2006/0251618 A1    Nov. 9, 2006

Related U.S. Application Data

(60) Provisional application No. 60/650,226, filed on Feb. 3, 2005.

(51) Int. Cl.
*A61F 2/01*   (2006.01)
*A61K 38/21*  (2006.01)

(52) U.S. Cl. .................. 424/422; 424/426; 424/85.4

(58) Field of Classification Search .............. None
See application file for complete search history.

(56) References Cited

U.S. PATENT DOCUMENTS

| | | | |
|---|---|---|---|
| 5,219,572 | A | 6/1993 | Sivaramakrishnan et al. |
| 5,728,396 | A | 3/1998 | Peery et al. |
| 5,904,935 | A | 5/1999 | Eckenhoff et al. |
| 5,932,547 | A | 8/1999 | Stevenson et al. |
| 5,972,370 | A * | 10/1999 | Eckenhoff et al. ......... 424/424 |
| 5,997,527 | A | 12/1999 | Gumucio et al. |
| 6,113,938 | A | 9/2000 | Chen et al. |
| 6,124,261 | A | 9/2000 | Stevenson et al. |
| 6,132,420 | A | 10/2000 | Dionne et al. |
| 6,235,712 | B1 | 5/2001 | Stevenson et al. |
| 6,270,787 | B1 | 8/2001 | Ayer |
| 6,287,295 | B1 | 9/2001 | Chen et al. |
| 6,375,978 | B1 | 4/2002 | Kleiner et al. |
| 6,468,961 | B1 | 10/2002 | Brodbeck et al. |
| 6,508,808 | B1 | 1/2003 | Carr et al. |
| 6,524,305 | B1 | 2/2003 | Peterson et al. |
| 6,544,252 | B1 | 4/2003 | Theeuwes et al. |
| 6,703,225 | B1 * | 3/2004 | Kojima et al. ............ 435/69.51 |
| 6,939,556 | B2 | 9/2005 | Lautenbach |
| 7,014,636 | B2 | 3/2006 | Gilbert |
| 7,074,423 | B2 | 7/2006 | Fereira et al. |
| 7,163,688 | B2 | 1/2007 | Peery et al. |
| 7,207,982 | B2 | 4/2007 | Dionne et al. |
| 7,258,869 | B1 | 8/2007 | Berry et al. |
| 2002/0197235 | A1 * | 12/2002 | Moran .................. 424/85.5 |
| 2003/0157178 | A1 | 8/2003 | Chen et al. |
| 2003/0170289 | A1 | 9/2003 | Chen et al. |
| 2003/0180364 | A1 | 9/2003 | Chen et al. |
| 2004/0157951 | A1 | 8/2004 | Wolf |
| 2004/0224903 | A1 * | 11/2004 | Berry et al. .................. 514/23 |
| 2005/0008661 | A1 | 1/2005 | Fereira et al. |
| 2005/0112188 | A1 | 5/2005 | Eliaz et al. |
| 2005/0175701 | A1 | 8/2005 | Pan et al. |
| 2005/0266087 | A1 * | 12/2005 | Junnarkar et al. .......... 424/488 |
| 2005/0276856 | A1 | 12/2005 | Fereira et al. |
| 2006/0193918 | A1 | 8/2006 | Rohloff et al. |
| 2006/0216242 | A1 | 9/2006 | Rohloff et al. |
| 2006/0246138 | A1 | 11/2006 | Rohloff et al. |
| 2006/0263433 | A1 * | 11/2006 | Ayer et al. .................. 424/489 |
| 2007/0281024 | A1 | 12/2007 | Lautenbach et al. |

FOREIGN PATENT DOCUMENTS

| | | |
|---|---|---|
| WO | 98/27962 | 7/1998 |
| WO | 98/27963 | 7/1998 |
| WO | 98/27963 A2 | 7/1998 |
| WO | 99/29306 | 6/1999 |
| WO | 99/29306 A1 | 6/1999 |
| WO | 00/29206 | 5/2000 |
| WO | 00/29206 A1 | 5/2000 |
| WO | 00/45790 | 8/2000 |
| WO | 00/45790 A2 | 8/2000 |
| WO | 02/36072 | 5/2002 |
| WO | 03/007981 | 1/2003 |
| WO | WO/03/007981 | * 1/2003 |
| WO | 03/041757 | 5/2003 |
| WO | 2004/056338 | 7/2004 |
| WO | 2004/056338 A2 | 7/2004 |
| WO | 2004/089335 | 10/2004 |
| WO | 2004/089335 A2 | 10/2004 |
| WO | 2006/084139 | 8/2006 |

OTHER PUBLICATIONS

Adolf GR, Human interferon omega-a review. Mult. Sclr., 1, S44-47, 1995.*
Roberts et al., J Interferon Cytokine Res. Oct. 1998;18(10):805-16, abstract only.
Tsung et al., J Pharm Sci, May 1997;86(5):603-7, abstract only.
Malley et al., Drug Chem Toxicol. Nov. 2001;24(4):315-38, abstract only.

* cited by examiner

*Primary Examiner*—Lorraine Spector
*Assistant Examiner*—Elly-Gerald Stoica
(74) *Attorney, Agent, or Firm*—Gary R. Fabian; Barbara G. McClung

(57) ABSTRACT

An implantable device includes a reservoir containing a suspension of an interferon in an amount sufficient to provide continuous delivery of the interferon at a therapeutically effective rate of 1 ng/day to 600 μg/day to maintain and achieve therapeutic blood or plasma levels of the interferon throughout a substantial period of the administration period.

33 Claims, 7 Drawing Sheets

IMPLANTABLE DEVICE FOR CONTINUOUS DELIVERY OF INTERFERON

CROSS-REFERENCE TO RELATED APPLICATIONS

This application claims priority from U.S. Provisional Application No. 60/650,226, filed Feb. 3, 2005, the content of which is incorporated herein by reference.

BACKGROUND OF THE INVENTION

The invention relates to delivery of interferon at controlled rates over extended periods of time.

Interferons are a group of glycoprotein cytokines produced by cells in response to various stimuli, such as exposure to virus, bacterium, parasite, or other antigen. Interferons have antiviral, immunomodulatory, and antiproliferative activities. Interferons are classified as Type I or Type II. Interferons classified as Type I bind to a common receptor called the Interferon Type I or α-β receptor and are produced by leukocytes, fibroblasts, or lymphoblasts in response to virus or interferon inducers. Interferon Type I includes interferon alpha (IFN-α), interferon beta (IFN-β), and interferon omega (IFN-ω), but IFN-ω has limited homology to human IFN-α (about 60%) and human IFN-β (about 29%). Interferons classified as Type II are produced by T-lymphocytes. Interferon Type II includes interferon gamma (IFN-γ). Interferons are used for treatment of viral hepatitis, multiple sclerosis, and certain cancers. IFN-ω in particular has been indicated for treatment of Hepatitis B & C populations. The injectable form of IFN-ω is currently in Phase II clinical studies for Hepatitis C. This injectable form is solution-based and is not formulated for sustained delivery.

There is interest in delivering interferons to patients in a controlled manner over a prolonged period without intervention. For instance, sustained delivery of IFN-ω can improve the therapeutic effect of IFN-ω by reduction or elimination of peak plasma-level related effects of multiple bolus injections, thereby potentially minimizing systemic side effects such as fatigue and flu-like symptoms. Sustained delivery of a beneficial agent without intervention can be provided by implantable drug delivery devices, e.g., osmotic, mechanical, or electromechanical pump implants, and depot injections. Implantable drug delivery devices are attractive for a number of reasons. For example, implantable drug delivery devices can be designed to provide therapeutic doses of the drug over periods of weeks, months, or even a year. Depot injections typically provide therapeutic doses over periods of weeks. Implantable drug delivery devices once inserted in the patient are not easily tampered with by the patient. Thus, patient compliance is generally assured.

Sustained delivery of an interferon requires the interferon to be contained within a formulation that is substantially stable at elevated temperature, e.g., 37° C. or higher, over the operational life of the implantable delivery drug device. Interferon is a biomolecular material, specifically a protein. Generally speaking, protein formulations that are stable at elevated temperature for a long duration, e.g., weeks, months, or a year, are difficult to design. Proteins are naturally active in aqueous environments. Therefore, it would be convenient to formulate proteins as aqueous solutions. Unfortunately, proteins are typically only marginally stable in aqueous formulations for a long duration. One reason for this is that proteins can degrade via a number of mechanisms, such as deamidation (usually by hydrolysis), oxidation, disulfide interchange, and racemization, and water is a reactant in many of these degradation pathways. Water also acts as a plasticizer and facilitates denaturation and/or aggregation of protein molecules.

Aqueous protein formulations may be reduced to particles using techniques such as freeze-drying or lyophilization, spray-drying, and desiccation. Such particle protein formulations may exhibit increased stability over time at ambient and even elevated temperature. However, there is the challenge of delivering particle formulations from an implantable drug delivery device at a controlled flow rate. It has been suggested to suspend particle protein formulations in non-aqueous, flowable vehicles to allow their delivery from an implantable drug delivery device. A suitable vehicle typically has a high viscosity, e.g., 1 kP or more, so that the particles can be uniformly dispersed in the suspension for a desired duration.

From the foregoing, there continues to be a need for a formulation of interferon that is stable at storage and delivery conditions for a desired duration and deliverable via an implantable drug delivery device.

SUMMARY OF THE INVENTION

In one aspect, the invention relates to a suspension formulation of interferon which comprises a non-aqueous, single-phase vehicle including at least one polymer and at least one solvent, the vehicle exhibiting viscous fluid characteristics, and an interferon contained in a particle formulation dispersed in the vehicle. The particle formulation includes a stabilizing component comprising one or more stabilizers selected from the group consisting of carbohydrates, antioxidants, and amino acids. The suspension formulation is characterized in that less than 10% of the interferon degrades over 3 months under an accelerated storage condition.

In another aspect, the invention relates to a method of treating an interferon-responsive disorder which comprises administering to a subject the suspension formulation described above.

Other features and advantages of the invention will be apparent from the following description.

BRIEF DESCRIPTION OF DRAWINGS

So that the above recited features and advantages of the invention can be understood in detail, a more particular description of the invention, briefly summarized above, may be had by reference to the embodiments thereof that are illustrated in the appended drawings. It is to be noted, however, that the appended drawings illustrate only typical embodiments of this invention and are therefore not to be considered limiting of its scope, for the invention may admit to other equally effective embodiments.

FIG. 3 shows percentage of main peak of IFN-ω as measured by Reversed Phase High Performance Liquid Chromatography (RP-HPLC) for particle formulations of IFN-ω before and after spray drying.

FIG. 4 shows main peak as measured by RP-HPLC for IFN-ω particle formulation suspended in LA/PVP vehicle.

DETAILED DESCRIPTION OF THE INVENTION

Figure 1:
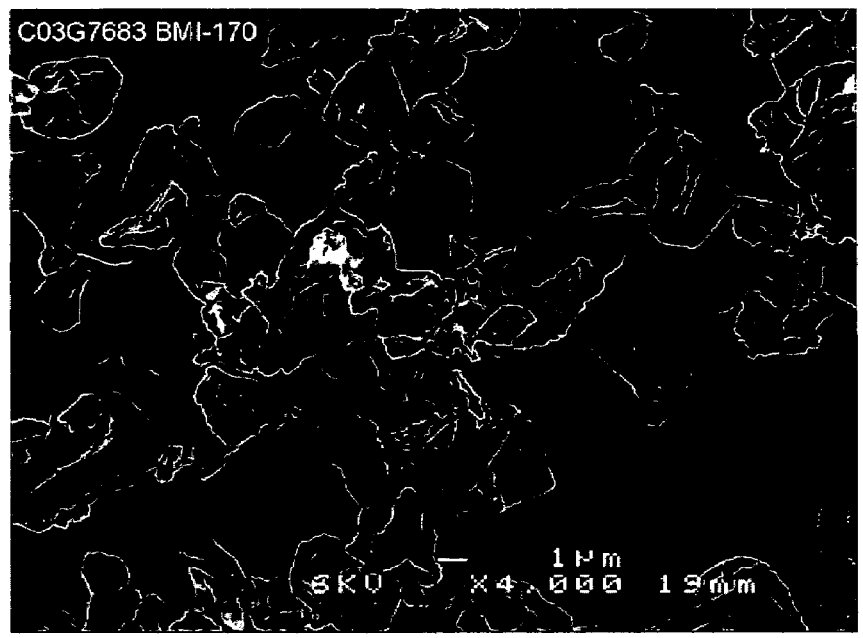
FIG. 1 shows a scanning electron microscope (SEM) image of spray dried particles.

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings and discussions that follow.

The invention provides particle formulations of interferon that can be used to prepare suspension formulations of interferon that are deliverable via sustained delivery systems, e.g., implantable drug delivery devices and depot injections. Interferons that may be included in particle formulations of the invention may be recombinant molecules that can activate the Interferon Type I receptor (α-β receptor) or Interferon Type II receptor. These recombinant molecules may or may not contain sequence homology to native human Type I or Type II interferons. Interferons according to embodiments of the invention may be selected from the group consisting of proteins having the biological activity of recombinant human interferon, interferon analogs, interferon isoforms, interferon mimetics, interferon fragments, hybrid interferon proteins, fusion protein oligomers and multimers of the above, homologues of the above, glycosylation pattern variants of the above, muteins of the above, and interferon molecules containing the minor modifications enumerated above. Interferons according to the invention shall not be limited by method of synthesis or manufacture and shall include those synthesized or manufactured by recombinant (whether produced from cDNA or genomic DNA), synthetic, transgenic, and gene-activated methods. Specific examples of interferons include, but are not limited to, IFN-α, IFN-β, IFN-ω, and IFN-γ.

Particle formulations of the invention are preferably chemically and physically stable for at least 1 month, more preferably at least 3 months, most preferably at least 6 months, at delivery temperature. The delivery temperature could be normal body temperature, e.g., 37° C., or slightly higher than normal body temperature, e.g., 40° C. Particle formulations of the invention are preferably chemically and physically stable for at least 3 months, more preferably at least 6 months, most preferably at least 12 months, at storage temperature. The storage temperature could be refrigeration temperature, e.g., around 5° C., or room temperature, e.g., around 25° C. The term "chemically stable" means that an acceptable percentage of degradation products produced by chemical pathways such as deamidation (usually by hydrolysis) or oxidation is formed. For example, a formulation may be considered chemically stable if less than 35%, preferably no more than 20%, breakdown products are formed after 3 months, preferably after 6 months, at delivery temperature and after 6 months, preferably after 12 months, at storage temperature. The term "physically stable" means that an acceptable percentage of aggregates (e.g., dimers and other higher molecular weight products) is formed. For example, a formulation may be considered physically stable if less than 10%, preferably no more than 3%, more preferably less than 1%, aggregates are formed after 3 months, preferably after 6 months, at delivery temperature and 6 months, preferably 12 months, at storage temperature.

Preferably, particle formulations of the invention are formable into particles using processes such as spray drying, lyophilization, desiccation, freeze-drying, milling, granulation, ultrasonic drop creation, crystallization, and precipitation. Preferably, the particles are uniform in shape and size to ensure consistent and uniform rate of release from the delivery device. Preferably, the particles are sized such that they can be delivered via an implantable drug delivery device. For example, in a typical osmotic pump implant having a delivery orifice, the size of the particles should be no greater than 30%, preferably no greater than 20%, more preferably no greater than 10%, of the diameter of the delivery orifice. It is also desirable that the particles when incorporated in a suspension vehicle do not settle within 3 months at delivery temperature. Generally speaking, smaller particles tend to have a lower settling rate in viscous suspension vehicles than larger particles. Therefore, micron- to nano-sized particles are typically desirable. For an osmotic pump implant having a delivery orifice diameter in a range from 0.1 to 0.5 mm, for example, particle sizes are preferably less than 50 μm, more preferably less than 10 μm, most preferably in a range from 3 to 7 μm.

The invention provides particle formulations of interferons possessing many or all of the characteristics described above. For example, particle formulations according to embodiments of the invention are chemically and physically stable at 40° C. for at least 6 months and at 5° C. and 25° C. for at least 12 months. We have found that particle formulations according to embodiments of the invention can be prepared by spray drying with high yield, e.g., greater than 50%, with average particle size typically less than 50 μm and moisture content typically below 5% by weight. Particle formulations according to embodiments of the invention may also be prepared by other suitable processes available in the art for forming particles from a mixture of components, such as lyophilization, freeze-drying, milling, granulation, ultrasonic drop creation, crystallization, precipitation, and dessication. Particle formulations according to embodiments of the invention preferably have a low moisture content, typically less than 5% by weight.

In one embodiment, a particle formulation includes an interferon as described above, one or more stabilizers, and optionally a buffer. The stabilizers may be carbohydrate, antioxidant and/or amino acid. The amounts of stabilizers and buffer in the particle formulation can be determined experimentally based on the activities of the stabilizers and buffers and the desired characteristics of the formulation. Carbohydrate, antioxidant, amino acid, and buffer levels are generally all of concern in creating a particle formulation according to the invention. Typically, the amount of carbohydrate in the formulation is determined by aggregation concerns. In general, the carbohydrate level should not be too high so as to avoid promoting crystal growth in the presence of water due to excess carbohydrate unbound to interferon. Typically, the amount of antioxidant in the formulation is determined by oxidation concerns, while the amount of amino acid in the formulation is determined by oxidation concerns and/or formability of particles during spray drying. Typically, the amount of buffer in the formulation is determined by pre-processing concerns, stability concerns, and formability of particles during spray drying. Buffer may be required to stabilize interferon during processing, e.g., solution preparation and spray drying, when all excipients are solubilized. However, care should be exercised in determining the amount of buffer. Too much buffer can produce a buffer system in the presence of water, which can then lead to crystallization.

Examples of carbohydrates that may be included in the particle formulation include, but are not limited to, monosaccharides, such as fructose, maltose, galactose, glucose, D-mannose, and sorbose, disaccharides, such as lactose, sucrose, trehalose, cellobiose, polysaccharides, such as raffinose, melezitose, maltodextrins, dextrans, and starches, and alditols (acyclic polyols), such as mannitol, xylitol, maltitol, lactitol, xylitol sorbitol, pyranosyl sorbitol, and myoinsitol. Preferred carbohydrates include non-reducing sugars, such as sucrose, trehalose, mannitol, and dextrans.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteins, thioglycerol, thioglycolic acid, thiosorbitol, butylated hydroxanisol, butylated hydroxyltoluene, and propyl gallate.

Examples of amino acids that may be included in the particle formulation include, but are not limited to, arginine, methionine, glycine, histidine, alanine, L-leucine, glutamic acid, Iso-leucine, L-threonine, 2-phenylamine, valine, norvaline, praline, phenylalanine, trytophan, serine, asparagines, cysteine, tyrosine, lysine, and norleucine. Preferred amino acids include those that readily oxidize, e.g., cysteine, methionine, and trytophan.

Examples of buffers that may be included in the particle formulation include, but are not limited to, citrate, histidine, succinate, phosphate, maleate, tris, acetate, carbohydrate, and gly-gly. Preferred buffers include citrate, histidine, succinate, and tris.

The particle formulation may include other excipients, such as surfactants, bulking agents, and salts. Examples of surfactants include, but are not limited to, Polysorbate 20, Polysorbate 80, PLURONIC® F68, and sodium docecyl sulfate (SDS). Examples of bulking agents include, but are not limited to, mannitol and glycine. Examples of salts include, but are not limited to, sodium chloride, calcium chloride, and magnesium chloride.

Table 1 below shows examples of particle formulation composition ranges of the invention.

TABLE 1

| | RANGE | PREFERRED RANGE | MOST PREFERRED RANGE |
|---|---|---|---|
| LOADING IN PARTICLE FORMULATION (WT %) | | | |
| Protein | 0.1 to 99.9% | 1 to 50% | 1 to 35% |
| Surfactant | 0.0 to 10% | 0.01 to 10% | 0.01 to 5% |
| Bulking Agent | 0 to 99.9% | 0 to 70% | |
| Salt | 0 to 99.9% | 0 to 70% | |
| STABILIZERS TO PROTEIN (WT RATIO) | | | |
| Carbohydrate | 0.1 to 99.9 | >0.5 | >1 |
| Antioxidant and/or amino acid | 0 to 99.9 | >0.5 | |

TABLE 1-continued

| | RANGE | PREFERRED RANGE | MOST PREFERRED RANGE |
|---|---|---|---|
| BUFFER | | | |
| Buffer to Protein (WT RATIO) | 0-3 | 1.5-2.5 | 1.7-2.2 |
| Concentration | 5 mM to 50 mM | 5 mM to 25 mM | 15 mM to 25 mM |
| pH | 5.0 to 8.0 | 5.5 to 6.5 | |

One particularly useful example of particle interferon formulations includes 1:2:1:1.5-2.5 interferon:carbohydrate:antioxidant and/or amino acid:buffer. The term "antioxidant and/or amino acid" refers to antioxidant alone or amino acid alone or a combination of antioxidant and amino acid. In another example, particle interferon of formulations 1:2:1:1.5-2.5 IFN-ω:sucrose:methionine:citrate were prepared.

As stated earlier, particle formulations of the invention may be prepared by known techniques such as spray drying, lyophilization, desiccation, or other technique available in the art for forming particles from a mixture of components. A typical spray dry process may include loading a spray solution containing a protein and stabilizing excipients into a sample chamber, which may be maintained at refrigeration to room temperature. Refrigeration generally promotes stability of the protein. A feed pump then sprays the spray solution into a nozzle atomizer. At the same time, atomized gas (typically, air, nitrogen, or inert gas) is directed at the outlet of the nozzle atomizer to form a mist of droplets from the spray solution. The mist of droplets are immediately brought into contact with a drying gas in a drying chamber. The drying gas removes solvent from the droplets and carries the particles into a collection chamber. In spray drying, factors that can affect yield include, but are not limited to, localized charges on particles, which could promote adhesion of the particles to the spray dryer, and aerodynamics of the particles, which could make it difficult to collect the particles. In general, yield of the spray dry process depends in part on the particle formulation. As will be demonstrated below, particle formulations of the invention can be effectively spray dried.

Figure 2:
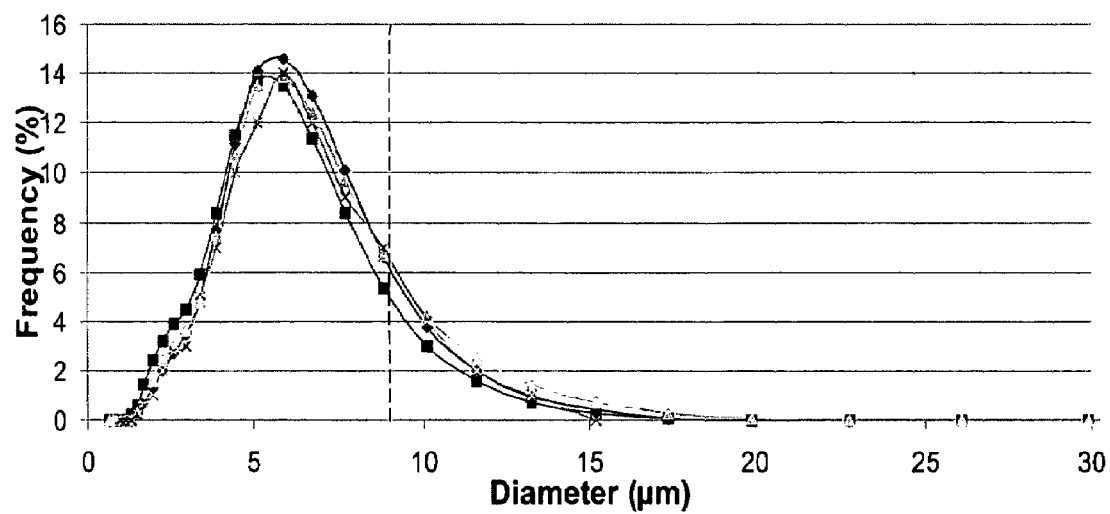
FIG. 2 shows particle size distribution for four different spray dry runs from spray solutions of particle formulations.

In one embodiment, spray dried particles were formed from spray solutions containing IFN-ω, sucrose (carbohydrate), methionine (amino acid), and citrate (buffer). In a preferred embodiment, IFN-ω, sucrose, methionine, and citrate are present in the solution in a ratio of 1:2:1:1.5-2.5 (IFN-ω:sucrose:methionine:citrate). FIG. 1 shows a SEM image for spray dried particles formed from a spray solution having IFN-ω:sucrose:methionine:citrate in a ratio of 1:2:1:2.15. The average particle size is 4-5 μm. The particles have buckled or raisin-like morphology. FIG. 2 shows particle size distributions of four different spray dry runs for a spray solution having IFN-ω:sucrose:methionine:citrate in a ratio of 1:2:1:2.15. FIG. 2 shows that IFN-ω formulations of the invention can be reproducibly spray dried with tight particle size distribution profiles.

Table 2 shows yield data for various spray-dried formulations of the invention. The results show that yield greater than 60% is achievable with IFN-ω particle formulations of the invention. In Table 2, "batch size" is starting solid material (g) in spray dry solution and "yield" is percent solid material captured after spray drying.

TABLE 2

| | IFN-ω | Sucrose | Methionine | Citrate | Batch Size | Yield |
|---|---|---|---|---|---|---|
| A | 1 | 2 | 1 | 1.7 | 16.1 g | 77.2% |
| B | 1 | 2 | 1 | 2.2 | 2.4 g | 60.6% |

The following examples further illustrate the invention. These examples are not intended to limit the invention as otherwise described herein.

In the examples below, stability samples were evaluated before and after spray drying using Reversed Phase High Performance Liquid Chromatography (RP-HPLC). RP-HPLC is used to monitor IFN-ω chemical stability. The main IFN-ω chemical degradation products (oxidized and deamidated forms) were separated from the native form using a reversed phase Zorbax 300SB-C8 column maintained at 55° C. Protein peaks were monitored by UV at 220 nm. The mobile phase involves a gradient elution, with solvent A: 0.1% trifluoroacetic acid in water, and solvent B: 0.08% trifluoroacetic acid in acetonitrile, and is pumped at the flow rate of 1.2 mL/min. For comparison purposes, stability samples were also evaluated for monomers using Size Exclusive Chromatography (SEC).

The stability samples were evaluated under long term storage and accelerated storage conditions. According to the International Conference on Harmonisation of Technical Requirements for Registration of Pharmaceuticals for Human Use Q1A(R2) guideline, long term stability condition is 25° C.±2° C./60% RH±5% RH for 12 months for the general case and 5° C.±3° C. for 12 months for drug substances intended for storage in a refrigerator. The accelerated storage condition is 40° C.±2° C./75% RH±5% RH for the general case and 25° C.±2° C./60% RH±5% RH for 6 months for drug substances intended for storage in a refrigerator.

It is desirable that particle IFN-ω formulations according to embodiments of the invention have oxidation level less than 7%, deamidation level less than 7%, and dimer level less than 3% after 3 months at accelerated storage condition (e.g., 40° C.±2° C./75% RH±5% RH) or 6 months at long term storage condition (e.g., 25° C.±2° C./60% RH±5% RH). These preferable oxidation and deamidation upper limits are based on impurity levels associated with the highest dosage of IFN-ω injected during Phase I and/or II clinical trials. The desired dimer upper limit is based on acceptable dimer levels associated with other proteins. The total aggregation after 6 months of accelerated storage is preferably less than 10%, more preferably less than 8%, most preferably less than 5%.

Example 1

Figures 3, 4:
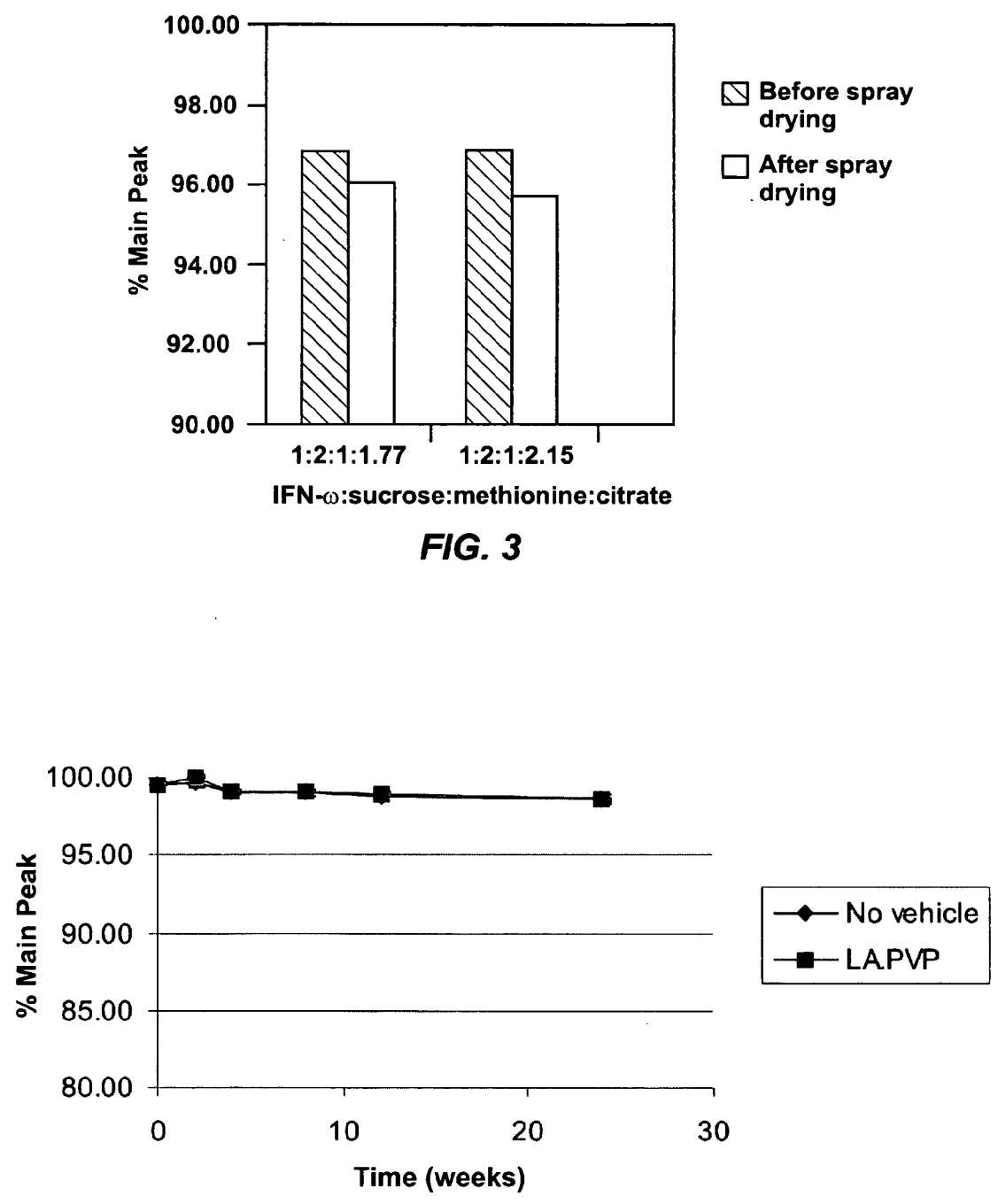

A bulk solution of IFN-ω was obtained as a frozen solution having a concentration of approximately 5 mg/ml. The IFN-ω solution was dialyzed against 25 mM citrate solution (pH 6.0). Sucrose and methionine in citrate solution were added to the dialyzed IFN-ω to make final IFN-ω:sucrose:methionine:citrate in a ratio of 1:2:1:1.77. The solution was spray dried as described above. The average particle size was 4-5 μm. The spray solution and spray dried particles were analyzed using RP-HPLC. The first two bars of FIG. 3 show percent main peak for the spray solution and spray dried particles of this example. Percent main peak refers to the fraction of IFN-ω detected that is in a monomeric form and does not appear to be chemically degraded in any form Example 2

A bulk solution of IFN-ω was obtained as a frozen solution having a concentration of approximately 5 mg/ml. The IFN-ω solution was dialyzed against 25 mM citrate solution (pH 6.0). Sucrose and methionine in citrate solution were added to the dialyzed IFN-ω to make final IFN-ω:sucrose:methionine:citrate in a ratio of 1:2:1:2.15. The solution was spray dried as described above. The average particle size was 4-5 μm. The spray solution and spray dried particles were analyzed using RP-HPLC. The second two bars of FIG. 3 show percent main peak for the spray solution and spray dried particles of this example.

Example 3

A bulk solution of IFN-ω was obtained as a frozen solution having a concentration of approximately 5 mg/ml. The IFN-ω solution was dialyzed against 25 mM citrate solution (pH 6.0). Sucrose and methionine in citrate solution were added to the dialyzed IFN-ω to make final IFN-ω:sucrose:methionine:citrate in a ratio of 1:2:1:2.2 at IFN-ω concentration of 3.3 mg/mL. The solution was spray dried as described above. The spray dried particles were evaluated using RP-HPLC and SEC at various timepoints during storage. The results are shown in Tables 3 and 4 below.

TABLE 3

| | Temperature (° C.) | Time (months) | SEC Monomer (Standard Deviation) | RP-HPLC Main Peak (Standard Deviation) | Protein Content (Standard Deviation) |
|---|---|---|---|---|---|
| A (n = 15) | | 0 | 100.00 (0.01) | 96.26 (0.39) | 16.11 (0.21) |
| B (n = 3) | 40 | 1 | 99.85 (0.00) | 96.99 (0.19) | 16.47 (0.07) |
| C (n = 3) | 40 | 2 | 99.90 (0.01) | 95.85 (0.01) | 16.16 (0.22) |
| D (n = 3) | 40 | 3 | 99.93 (0.02) | 96.45 (0.35) | 16.51 (0.22) |
| E (n = 3) | 40 | 6 | 99.88 (0.00) | 95.24 (0.12) | 17.01 (0.13) |
| F (n = 3) | 25 | 6 | 99.93 (0.01) | 96.20 (0.10) | 17.14 (0.14) |
| G (n = 3) | 25 | 12 | 99.93 (0.01) | 96.15 (0.12) | 17.46 (0.14) |
| H (n = 3) | 5 | 6 | 99.93 (0.02) | 96.03 (0.11) | 16.92 (0.05) |
| I (n = 3) | 5 | 12 | 99.96 (0.01) | 96.15 (0.03) | 17.50 (0.11) |

TABLE 4

|  | Temperature (° C.) | Time (months) | Dimers % (Standard Deviation) | Oxidation % (Standard deviation) | Deamidation (Standard deviation) | Total aggregation |
|---|---|---|---|---|---|---|
| A (n = 15) |  | 0 | 0.00 (0.00) | 2.20 (0.11) | 1.53 (0.46) | 3.73 |
| B (n = 3) | 40 | 1 | 0.15 (0.00) | 1.98 (0.02) | 1.03 (0.02) | 3.16 |
| C (n = 3) | 40 | 2 | 0.15 (0.00) | 2.60 (0.03) | 1.56 (0.03) | 4.31 |
| D (n = 3) | 40 | 3 | 0.07 (0.02) | 2.13 (0.16) | 1.43 (0.20) | 3.63 |
| E (n = 3) | 40 | 6 | 0.12 (0.00) | 2.83 (0.12) | 1.93 (0.03) | 4.88 |
| F (n = 3) | 25 | 6 | 0.07 (0.01) | 2.71 (0.08) | 1.09 (0.02) | 3.87 |
| G (n = 3) | 25 | 12 | 0.07 (0.01) | 2.10 (0.11) | 1.75 (0.01) | 3.92 |
| H (n = 3) | 5 | 6 | 0.07 (0.02) | 2.77 (0.09) | 1.20 (0.02) | 4.04 |
| I (n = 3) | 5 | 12 | 0.04 (0.01) | 2.19 (0.01) | 1.66 (0.02) | 3.89 |

Table 3 shows that monomer and main peak were more than 99.8% and 86.5%, respectively, over the stability temperatures and times studied. Table 3 shows that protein content is relatively stable over time. Table 4 shows that dimer, oxidation, and deamidation levels were less than 0.2%, 2.9%, and 2%, respectively, over the stability temperatures and times studied. For comparison purposes, the bulk IFN-ω initially had approximately 1.5% oxidation level, 1.5% deamidation level, and 0% dimer level. Table 4 also shows that the total aggregation after 6 months of accelerated storage (formulation E) is less than 5%.

Example 4

Lyophilized IFN-ω particle formulations (IFN-ω:sucrose:methionine:citrate in a ratio of 1:2:1:0, 20 mM citrate, pH 6.0) were analyzed using RP-HPLC at various timepoints under long term and accelerated storage conditions. The results are shown in Table 5. The results show that IFN-ω remained stable even after 24 weeks at long term and accelerated storage conditions.

TABLE 5

|  | Temperature (° C.) | Time (weeks) | RP-HPLC Main Peak (Standard Deviation) |
|---|---|---|---|
| 1 | 4 | 0 | 99.61 (0.04) |
| 2 | 4 | 4 | 99.35 (0.02) |
| 3 | 4 | 8 | 100.00 (0.00) |
| 4 | 4 | 12 | 99.62 (0.02) |
| 5 | 4 | 24 | 99.53 (0.07) |
| 6 | 40 | 0 | 99.61 (0.04) |
| 7 | 40 | 2 | 99.75 (0.43) |
| 8 | 40 | 4 | 99.12 (0.07) |
| 9 | 40 | 8 | 99.04 (0.28) |
| 10 | 40 | 12 | 98.86 (0.07) |
| 11 | 40 | 24 | 98.67 (0.31) |
| 12 | 65 | 0 | 99.61 (0.04) |
| 13 | 65 | 2 | 97.82 (0.17) |
| 14 | 65 | 4 | 96.87 (0.04) |

The invention also provides suspension formulations of interferon that are deliverable via sustained release systems, e.g., implantable drug delivery devices and depot injections. The suspension formulations include particle formulations of interferon as described above suspended in vehicles. A vehicle according to an embodiment of the invention includes at least a polymer and a solvent combined together to provide a single-phase material that is biocompatible and non-aqueous. The suspension formulations of the invention are stable at elevated temperature and are deliverable via a sustained release system over a prolonged period.

The polymers and solvents used in vehicles according to embodiments of the invention are chosen to provide a homogeneous system that is both physically and chemically uniform throughout, for example, as determined by differential scanning calorimetry (DSC). To achieve a biocompatible vehicle, the polymers and solvents used in a vehicle according to the invention are chosen and combined such that the resultant vehicle disintegrates or breaks down over a period of time in response to a biological environment. The breakdown of the vehicle in a biological environment may take place by one or more physical or chemical processes, such as by enzymatic action, oxidation, reduction, hydrolysis (e.g., proteolysis), displacement, or dissolution by solubilization, emulsion or micelle formation. After a vehicle of the invention is broken down in a biological environment, components of the vehicle are then absorbed or otherwise dissipated by the body and surrounding tissue.

In one embodiment, the vehicle includes any pharmaceutically-acceptable polymer that can be combined with a pharmaceutically-acceptable solvent to provide a vehicle that is single-phase, biocompatible, suitable for creating and maintaining a suspension of a beneficial agent, and capable of providing a stable formulation of a beneficial agent. The polymer may be biodegradable or non-biodegradable. Preferably, the polymer is somewhat soluble in water. Examples of polymers useful in forming the vehicle include, but are not limited to, pyrrolidones, e.g., polyvinylpyrrolidone (PVP) having a molecular weight of 2,000 to 1,000,000, methylcellulose, carboxy methylcellulose, polylactides, polyglycolides, polylactide-co-glycolide, polylactic acids, polyglycolic acids, polyoxyethylene polyoxypropylene block copolymers (exhibiting a high viscosity at elevated temperatures, e.g., 37° C.) such as PLURONIC® 105, and esters or ethers of unsaturated alcohols such as vinyl acetate. If desired, more than one different polymer or grades of single polymer may be used to achieve a vehicle according to the invention.

In one embodiment, the vehicle includes any pharmaceutically-acceptable solvent that can be combined with a pharmaceutically-acceptable polymer to provide a vehicle that is single-phase, biocompatible, suitable for creating and maintaining a suspension of a beneficial agent, and capable of providing a stable formulation of a beneficial agent. The solvent may or may not be water soluble. Examples of solvents that may be used to provide a vehicle according to the present invention include, but are not limited to, benzyl benzoate (BB), benzyl alcohol (BA), lauryl lactate (LL), CERAPHYL® 31 (C31), lauryl alcohol (LA), polyethylene glycols (PEGs), glycofural (GF), vitamin E, and DMSO. Where desired, two or more solvents may be used to provide a vehicle according to the invention. In particular, two or more solvents may be required to provide a vehicle that facilitates the production of a stable formulation of a chosen beneficial agent.

The amount of polymer(s) and solvent(s) included in a vehicle according to the invention may be varied to provide the vehicle with desired performance characteristics. Generally speaking, a vehicle according to the invention will include about 40% to 80% (w/w) polymer(s) and about 20% to 60% (w/w) solvent(s). Presently preferred embodiments of a vehicle according to the invention include vehicles formed of polymer(s) and solvent(s) combined at the following ratios: about 25% solvent and about 75% polymer; about 30% solvent and about 70% polymer; about 35% solvent and about 65% polymer; about 40% solvent and about 60% polymer; about 45% solvent and about 55% polymer; and about 50% solvent and about 50% polymer (with all percentages given in w/w ratios).

The vehicle may also include one or more surfactants. For example, surfactants may be included in the vehicle to facilitate release of a beneficial agent suspended in the vehicle once the suspension formulation is delivered to an environment of use. Alternatively, surfactants may be included in the vehicle to help maintain the stability of a beneficial agent suspended in the vehicle. Examples of surfactants that may be used in the vehicle include, but are not limited to, esters of polyhydric alcohols such as glycerol monolaurate, ethoxylated castor oil, polysorbates, esters or ethers of saturated alcohols such as myristyl lactate, CERAPHYL® 50, polyoxyethylenepolyoxypropylene block copolymers, TWEENs, SPANs, glyceryl caprylate, glyceryl laurate, PEG-8 caprylic capric glycerides, polyglyceryl-6 oleate, dioctyly sodium, sulfosuccinate, and Vitamin E TPGS. Where included, the surfactant(s) will typically account for less than about 20% (w/w), preferably less than 10% (w/w), more preferably less than 5% (w/w) of the vehicle.

The vehicle may also include one or more preservatives. Preservatives that may be used in the vehicle include, for example, antioxidants and antimicrobial agents. Examples of potentially useful antioxidants include, but are not limited to, tocopherol (vitamin E), ascorbic acid, ascorbyl palmitate, butylated hydroxyanisole, butylated hydroxytoluene, and propyl gallate. Where one or more preservatives are incorporated in the vehicle, the amount used will vary depending on the application, the preservative used, and the desired result. Generally, a preservative is included only in amounts sufficient to achieve the desired preservative effect.

A vehicle according to the invention may be a Newtonian or a non-Newtonian material, and the viscosity of the vehicle will vary. In each embodiment, however, a vehicle according to the invention is formulated to provide a viscosity that is capable of maintaining a desired suspension of a chosen particle formulation of interferon over a predetermined period of time, thereby facilitating creation of a suspension formulation tailored to provide controlled delivery of the interferon at a desired rate. Therefore, the viscosity of a vehicle according to the invention will vary depending on, among other factors, the desired application, the size and type of the dry particle formulation to be included in the vehicle, and the required vehicle loading. The viscosity of a vehicle according to the invention can be varied, as desired, by altering the type or relative amounts of solvent and polymer materials included in the vehicle. In one embodiment, the vehicle of the invention is formulated as a viscous vehicle, with the vehicle having a viscosity in the range of about 1 kP to 10,000 kP. Where the vehicle of the invention is formulated as a viscous vehicle, the viscosity of the vehicle preferably ranges from about 10 kP to 250 kP.

A vehicle according to the invention is preferably manufactured by combining the desired ingredients without the addition of water. Generally, vehicles according to the invention may be prepared by combining the dry (e.g., powdered or low moisture content) ingredients in a dry box or under other dry conditions and blending them at an elevated temperature, preferably about 40° C. to 70° C., to allow them to liquefy and form a single phase. Where the vehicle includes a surfactant, the solvent portion of the vehicle is preferably combined with the surfactant at an elevated temperature before the desired polymer material is added for blending. Blending of the ingredients can be accomplished using any suitable equipment, such as a dual helix blade mixer, and blending is preferably completed under vacuum to remove trapped air bubbles produced from the dry ingredients. Once a liquid solution of the vehicle ingredients is achieved, the liquid vehicle may be allowed to cool to room temperature. If desired, the liquid vehicle may be removed from the blending apparatus to allow for cooling. Differential scanning calorimetry may be used to verify that the components included in the vehicle have been combined such that a single-phase material is formed. The final moisture content of the vehicle is preferably less than 5 wt %.

A vehicle may be loaded with varying amounts of interferon that allows for dosing of the interferon over time. The amount of interferon included in a suspension formulation depends on, among other factors, the potency of the interferon, the desired duration of treatment, and the desired release rate of the interferon. Typically, a particle formulation of interferon accounts for between about 0.1% to 50% (w/w) of a suspension formulation according to the invention, with the vehicle accounting for between about 50% and 99.9% (w/w). In a preferred embodiment, a suspension formulation according to the invention includes between about 0.1% and 30% (w/w) of the particle formulation. In a more preferred embodiment, a suspension formulation according to the invention includes between 1% and 20% (w/w) of the particle formulation.

A particle formulation as described above may be dispersed in a vehicle as described above using any mixing, blending, or other dispersion technique that provides a suspension formulation having a desired distribution of the particle formulation. Preferably the particle formulation is dispersed within the vehicle using a process that does not require the addition of water. For instance, the particle formulation can be dispersed within a vehicle according to the invention by combining the vehicle with the particle formulation under dry conditions and blending the materials under vacuum at an elevated temperature, preferably about 40° C. to 70° C., until a desired dispersion of the particle formulation within the vehicle is achieved. The particle formulation and the vehicle may be blended using the same equipment and techniques used to blend the vehicle. In particular, a mixer, such as a dual helix blade or similar mixer, may be used to blend the particle formulation and vehicle to achieve a suspension formulation according to the invention. After blending at elevated temperatures, the resulting suspension formulation is allowed to cool to room temperature. After preparation, the suspension formulation may be sealed in a dry container to avoid undesired incorporation of moisture.

Suspension formulations of the invention are stable when maintained at elevated temperatures and serve to minimize the potential for partial or complete occlusion of the delivery passage of a delivery device from which the formulations are delivered. In preferred embodiments, the suspension formulation of the invention is formulated such that it remains chemically and physically stable for at least 3 months at delivery temperature and for at least 6 months at storage temperature. The delivery temperature could be normal body temperature, e.g., 37° C., or slightly higher than normal body temperature, e.g., 40° C. The storage temperature could be refrigeration temperature, e.g., around 5° C., or room temperature, e.g., around 25° C. The term "chemically stable" means that an acceptable percentage of degradation products produced by chemical pathways such as deamidation (usually by hydrolysis) or oxidation is formed. For example, a suspension formulation may be considered chemically stable if less than 35%, preferably no more than about 20%, and most preferably less than 10% breakdown products are formed after 3 months at delivery temperature and after 6 months at storage temperature. The term "physically stable" means that an acceptable percentage of aggregates (e.g., dimers and other higher molecular weight products) is formed. For example, a suspension formulation may be considered physically stable if less than 15%, preferably no more than 10%, more preferably less than 3%, aggregates are formed after 3 months at delivery temperature and 6 months at storage temperature.

In preferred embodiments, an interferon is chemically stable and bioactive after suspension in a vehicle of the invention for at least 3 months at 40° C. The term "bioactive" means that the interferon has biological activity as defined by clinical efficacy or an in vitro technique that shows activity. A cell-based assay may be used to demonstrate that the interferon is bioactive, i.e., has the ability to kill a specific type of virus. In preferred embodiments, soluble interferon is released from the formulation exiting a delivery device at target levels. For pump implants, few pumping failures are encountered during operation and implant can be manufactured aseptically with minimal bubbles in the suspension formulation. In preferred embodiments, adverse toxicity reactions are not detected from the suspension formulation.

Suspension formulations according to embodiments of the invention may be formulated for delivery from an implantable drug delivery device. The implantable drug delivery device may be embodied by any such device capable of delivering a flowable formulation at a controlled rate over a sustained period after implantation within a subject. One example of a suitable implantable drug delivery device is an osmotic pump implant, such as DUROS® pump developed by ALZA Corporation. Non-osmotic pump implants may also be used. The suspension formulation may be formulated for delivery at flow rates up to 5 ml/day, depending on the interferon to be delivered and the implantable drug delivery device used to deliver the suspension formulation. Where the interferon is delivered from an osmotic pump implant designed to provide low flow rates, the formulation is preferably formulated for delivery of between 0.25 and 5 μL/day, more preferably for delivery of between 0.5 and 2.0 μL/day, and most preferably for delivery between 1.0 and 1.5 μL/day. In one embodiment, a suspension formulation according to an embodiment of the invention is formulated to deliver interferon from an implanted device in a range from 1 ng/day to 600 μg/day over one month, preferably over three months, more preferably over 6 months, much more preferably over 9 months, and most preferably over one year.

In one embodiment, a suspension formulation of interferon is formed by dispersing a particle formulation of interferon as described above in a suspension vehicle as described above. Table 6 below shows dosage examples of suspension formulation of interferon for sustained delivery via an implantable drug delivery device. In a preferred embodiment, an implantable drug delivery device contains 0.5 to 2.5 mg IFN, e.g., IFN-ω, for sustained delivery at a delivery rate in a range from 0.25 to 5 μL/day, more preferably from 0.5-2.0 μL/day, most preferably from 1.0 to 1.5 μL/day

TABLE 6

| MATERIAL | DOSAGE 1 | DOSAGE 2 |
|---|---|---|
| IFN-ω | 2.3 mg (1.5%) | 0.9 mg (0.6%) |
| Benzyl Benzoate, USP | 69.8 mg (45.0%) | 73.9 mg (47.7%) |
| Povidone, USP | 71.0 mg (45.8%) | 75.3 mg (48.6%) |
| Sucrose, NF | 4.6 mg (3.0%) | 1.8 mg (1.2%) |
| Methionine, USP | 2.3 mg (1.5%) | 0.9 mg (0.6%) |
| Sodium citrate, USP | 4.5 mg (2.9%) | 1.8 mg (1.2%) |
| Citric Acid Monohydrate, USP | 0.5 mg (0.3%) | 0.2 mg (0.1%) |

The following stability examples are presented for illustration purposes and are not to be construed as limiting the invention as otherwise described herein.

A study was conducted to assess the stability of a particle formulation of IFN-ω suspended in a vehicle that is biocompatible, single-phase, and non-aqueous. The samples were analyzed using Size Exclusion Chromatography (SEC) and Reversed Phase High Performance Liquid Chromatography (RP-HPLC). For the analysis, IFN-ω is extracted from the suspension using 50:50 (v/v) of methylene chloride:acetone. The solvent dissolves the vehicle in the suspension and precipitates the protein. After several times of washing with the same solvent mixture, the protein precipitate is dried and then reconstituted in water for analysis. The monomeric and aggregated forms of IFN-ω were separated by the SEC method using TSK Super SW2000 column and detected with UV detection at 220 nm. The purity and identity of IFN-ω were determined by RP-HPLC on a Zorbax 300SB-C8 RP-HPLC column, at acidic pH and with UV detection at 220 nm.

Example 5

IFN-ω particle formulation (IFN-ω:sucrose:methionine:citrate in a ratio of 1:2:1:2.15) was suspended in LA/PVP vehicle with a target particle loading of approximately 10% (w/w). The average particle size of the IFN-ω particle formulation was 4-5 μm. Reservoirs of several osmotic pump implants, such as DUROS® pump developed by ALZA Corporation, were each filled with approximately 150-μL of the suspension. A cap with an orifice (e.g. diffusion moderator) was affixed to the open end of each reservoir, and the implants were placed into a stoppered and crimped glass vial for storage at 40° C. up to 24 weeks. Samples were extracted and analyzed at initial, 1, 2, 3 and 6 months using RP-HPLC. FIG. 4 shows percent main peak as a function of time. Percent main peak refers to the fraction of IFN-ω detected that is in a monomeric form and does not appear to be chemically degraded in any form. The results show that IFN-ω suspended in LA/PVP vehicle is stable out to 4 weeks at 40° C. For comparison purposes, FIG. 4 also shows percent main peak for the IFN-ω particle formulation without the vehicle.

Example 6

Figure 5:
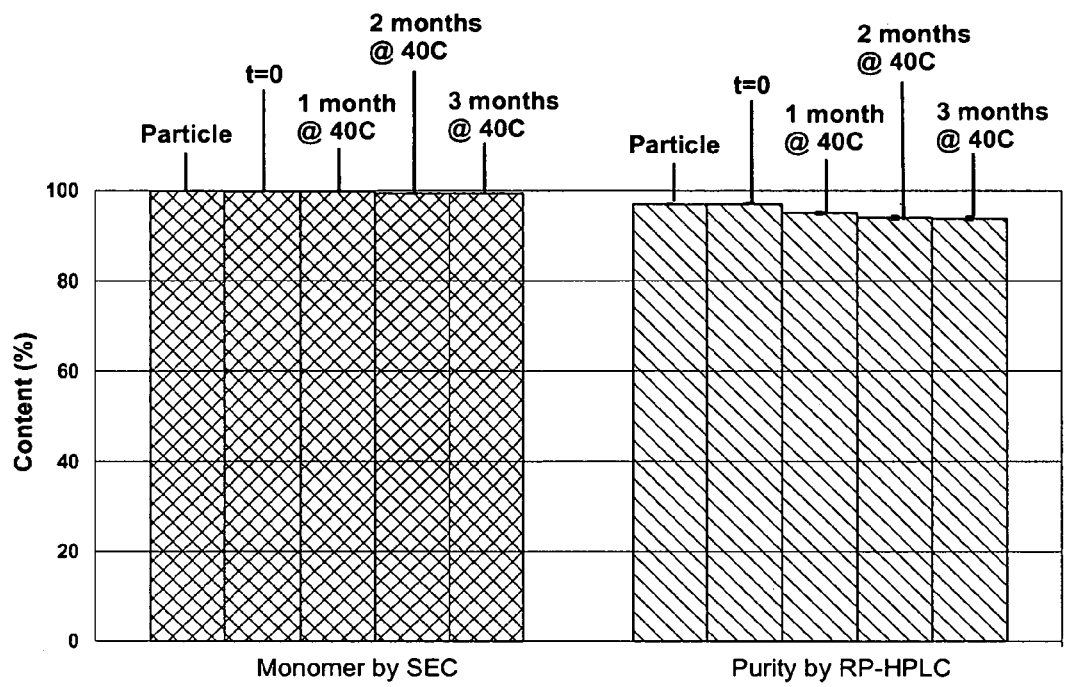
FIG. 5 shows monomer and purity levels at various time points for IFN-ω particle formulation suspended in CERAPHYL® 31/PVP vehicle.

IFN-ω particle formulation (IFN-ω:sucrose:methionine:citrate in a ratio of 1:2:1:2.15) was suspended in CERAPHYL® 31/PVP vehicle with a target particle loading of approximately 10% (w/w). Reservoirs of several osmotic pump implants, such as such as DUROS® pump developed by ALZA Corporation, were filled with approximately 150 μL of the suspension and stored at 40° C. for 3 months. The samples were extracted and analyzed at initial, 1 month, 2 months, and 3 months. FIG. 5 shows monomer level as measured by SEC and purity level as measured by RP-HPLC. As shown in FIG. 5, the suspension was relatively stable over 3 months at 40° C.

Example 7

Figure 6:
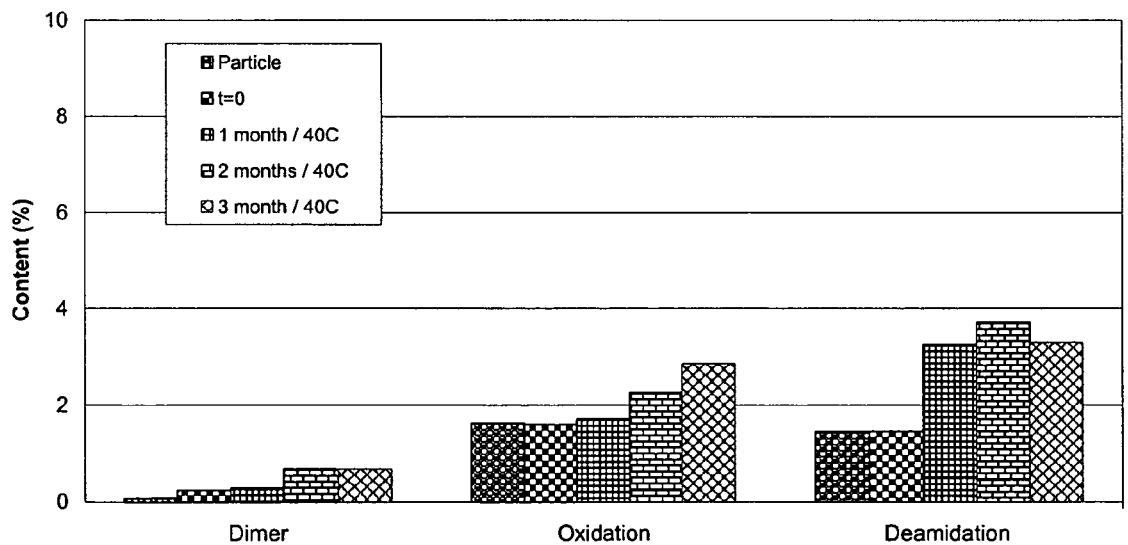
FIG. 6 shows stability results for IFN-ω particle formulation suspended in CERAPHYL® 31/PVP vehicle.

The reservoir of an osmotic pump implant, such as DUROS® pump, was loaded with approximately 150 μL of the suspension described in EXAMPLE 6 and stored at 5° C. for 6 months (storage conditions). FIG. 6 shows the stability results. The results show that IFN-ω suspended in Ceraphyl® 31/PVP vehicle is stable when stored at 5° C. for 6 months. At 6 months, percent degradation products from oxidation was less than 2%, deamidation was about 2%, other related proteins was less than 9%, and dimers was less than 0.5%. A slight increase in percent degradation products from deamidation and dimers was observed under storage conditions, while percent degradation products from oxidation remained substantially unchanged. The percent degradation products from oxidation, deamidation, other related proteins, and dimers indicate that the suspension was relatively stable under storage conditions for 6 months.

Example 8

Figure 7:
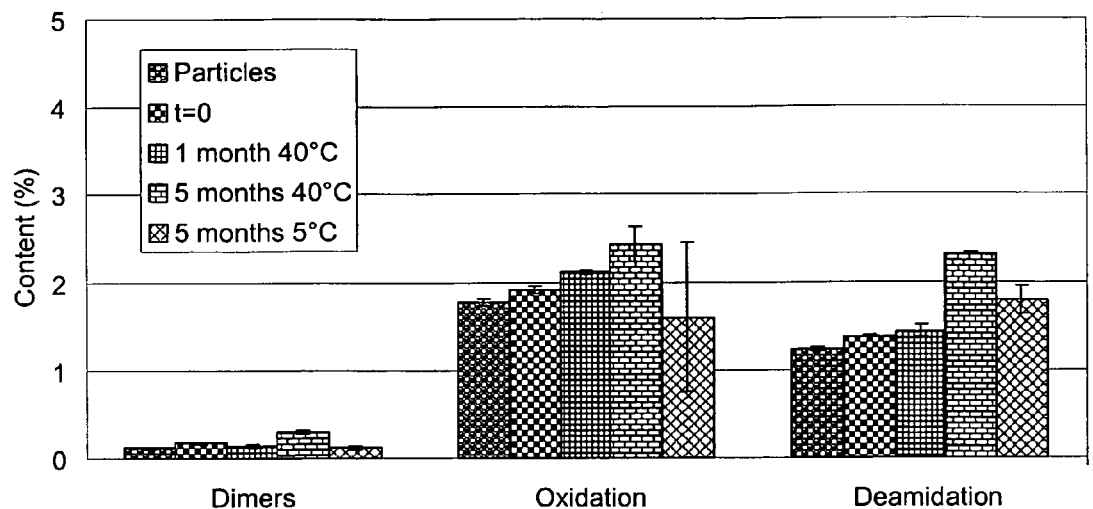
FIG. 7 shows stability results for IFN-ω particle formulation suspended in BB/PVP vehicle.

IFN-ω particle formulation (IFN-ω:sucrose:methionine: citrate in a ratio of 1:2:1:2.15) was suspended in BB/PVP vehicle with a target particle loading of approximately 10% (w/w). Reservoirs of several osmotic pump implants, such as DUROS® pump, were each filled with approximately 150 μL of the suspension. Some of the implants were stored at 40° C. for 161 days, while others were stored at 5° C. for 161 days. Samples were extracted and analyzed at initial, one and six months days using RP-HPLC. The stability results are shown in FIG. 7. Relative stability out to six months are shown in FIG. 7.

Example 9

Figure 8A:
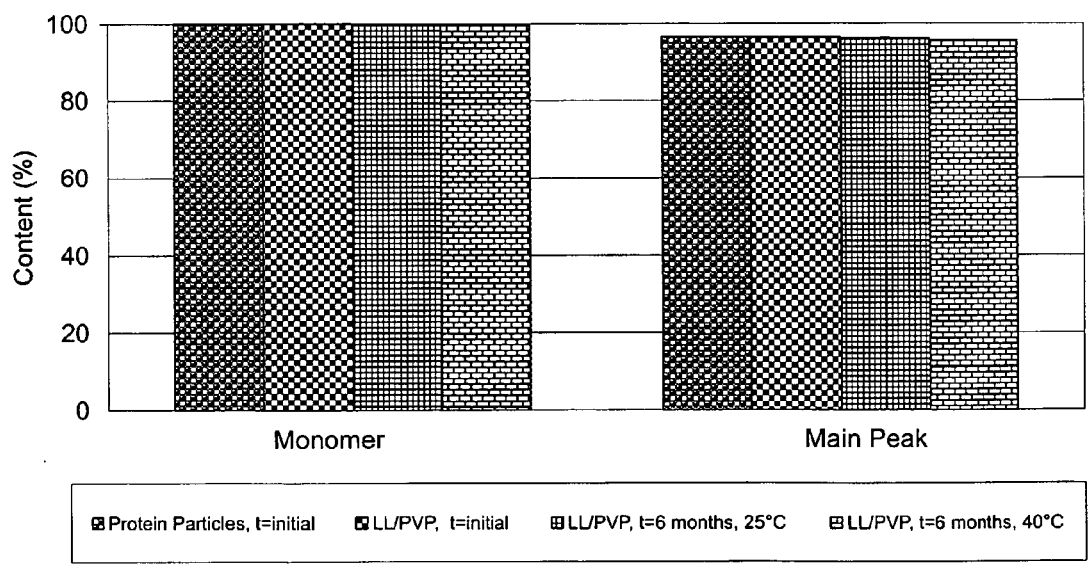
FIG. 8A shows stability of IFN-ω in LL/PVP vehicle after 6-month storage at 40° C.
Figure 8B:
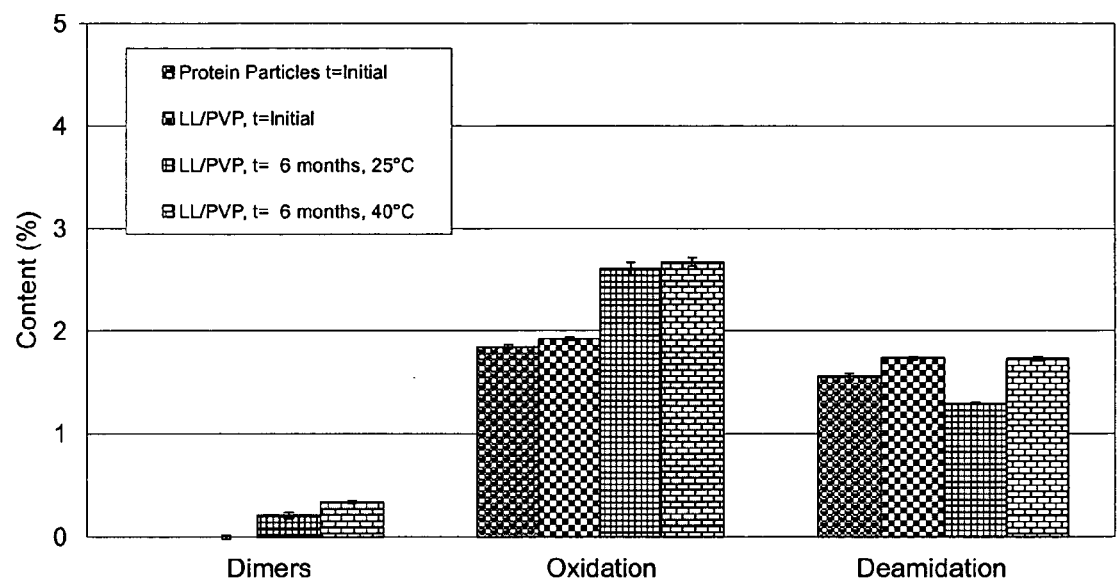
FIG. 8B shows stability of IFN-ω against degradation in LL/PVP vehicle after 6-month storage at 40° C.
Figure 8C:
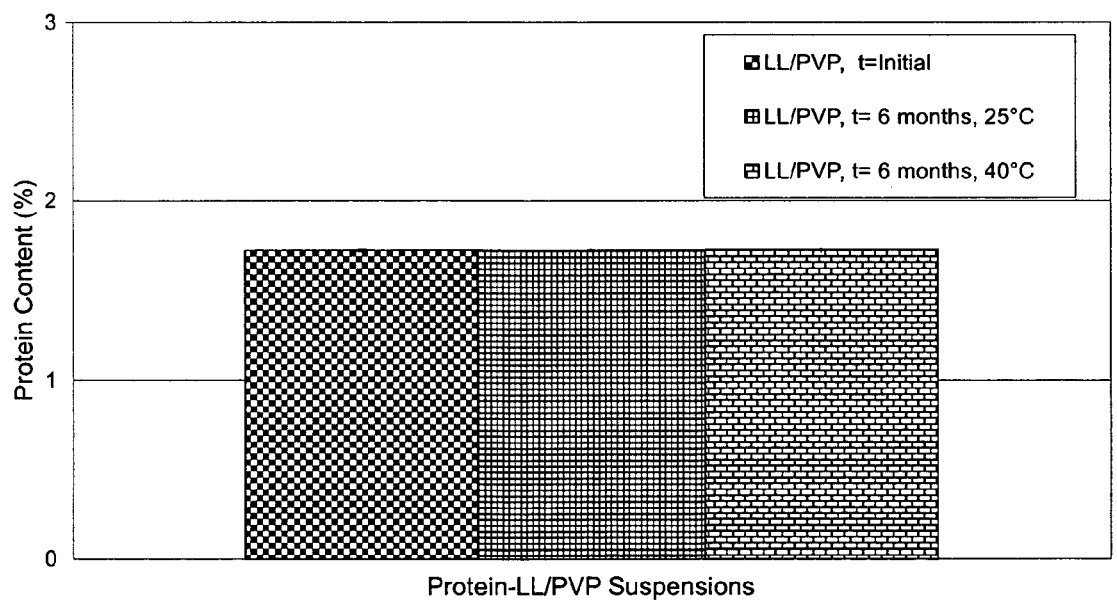
FIG. 8C shows protein content stability in LL/PVP vehicle after 6-month storage at 40° C.

Particle formulation of IFN-ω (IFN-ω:sucrose:methionine:citrate in a ratio of 1:2:1:2.15) was suspended in LL/PVP vehicle with a target particle loading of approximately 10% (w/w). Reservoirs of several osmotic pump implants, such as DUROS® pump, were filled with approximately 150 μL of the suspension and stored at 5° C., 25° C., or 40° C. for 180 days or 12 months. Samples were extracted and analyzed at various time points between initial and 180 days or 12 months using SEC or RP-HPLC. FIG. 8A shows stability of IFN-ω particle formulation in LL/PVP vehicle after storage of 6 months at 40° C. FIG. 8B shows percent degradation products from dimers, oxidation, deamidation, and other related proteins after storage of the suspension formulation for 6 months at 40° C. FIG. 8C shows protein content stability in LL/PVP vehicle after storage of 6 months at 40° C.

The following release rate examples are presented for illustration purposes and are not to be construed as limiting the invention as otherwise described herein.

A study was conducted to assess the release rate of suspension formulations according to embodiments of the invention using an implantable delivery device. The implantable delivery device selected for use is an osmotic pump, such as DUROS® pump developed by Alza Corporation. The osmotic pump includes a cylinder, made of titanium, having open ends. A diffusion moderator is mounted at a first end of the cylinder, and a semipermeable membrane is mounted at a second end of the cylinder. The diffusion moderator has a delivery conduit which allows fluid delivery from the interior to the exterior of the cylinder. The delivery conduit may be straight or spiral in shape. The semipermeable membrane forms a fluid-permeable barrier between the exterior and interior of the cylinder. A piston inside the cylinder defines a first compartment, which contains an osmotic agent, and a second compartment, which serves as the drug reservoir.

For the study, drug reservoirs of several osmotic pumps, such as DUROS® pumps, were filled with 150-μL of suspension formulation. The membrane ends of the osmotic pumps were placed into stoppered glass vials filled with 3 mL phosphate buffer solution (PBS), and the diffusion moderator ends of the osmotic pumps were placed into glass vials filled with 2.5 to 3 mL release rate medium (citrate buffer solution at pH 6.0 with 0.14 M NaCl and 0.2% sodium azide). The systems were placed into capped test tubes, with the diffusion moderator side down, and partially immersed in a 37° C. water bath. At specified time points, the glass vials at the diffusion moderator ends were replaced with new glass vials filled with 2.5 to 3 mL release rate medium (citrate buffer solution at pH 6.0 with 0.14 M NaCl and 0.2% sodium azide). Samples were collected from the diffusion moderator ends of the osmotic pumps and analyzed using RP-HPLC.

Example 10

Figure 9:
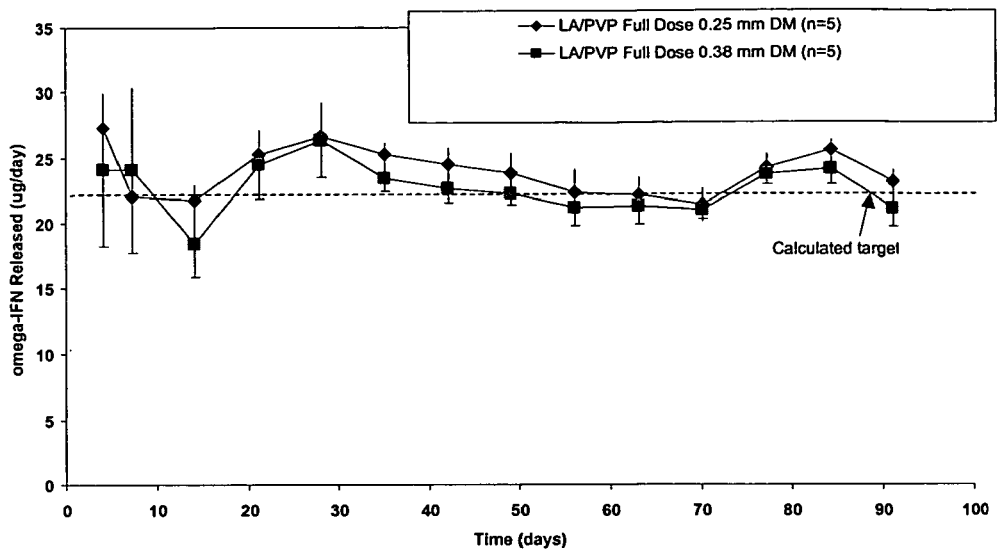
FIG. 9 shows release rate for IFN-ω particle formulation suspended in LA/PVP from osmotic pumps.

Drug reservoirs of several osmotic pumps were filled with approximately 150 μL of suspension formulation as prepared in EXAMPLE 5, i.e., IFN-ω particle formulation (IFN-ω: sucrose:methionine:citrate in a ratio of 1:2:1:2.15) suspended in LA/PVP. Diffusion moderators with straight delivery conduits having a diameter of 0.25 mm and 0.38 mm and a length of 1.5 mm were used. FIG. 9 shows the release rate per day out to 90 days at 37° C. The release rate data indicate that the systems deliver IFN-ω near the target rate of 22 μg/day out to 90 days at 37° C.

Example 11

Figure 10:
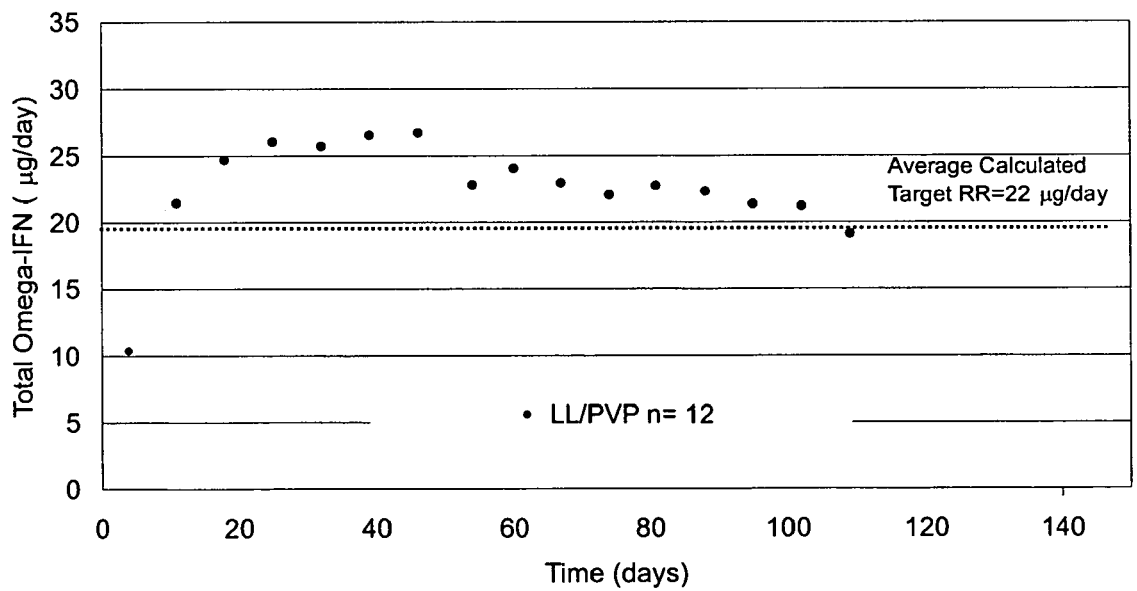
FIG. 10 shows release rate for IFN-ω particle formulation suspended in LL/PVP from osmotic pumps.

Drug reservoirs of several osmotic pumps were filled with approximately 150 μL of suspension formulation as prepared in EXAMPLE 6, i.e., IFN-ω particle formulation (IFN-ω: sucrose:methionine:citrate in a ratio of 1:2:1:2.15) suspended in LL/PVP. Diffusion moderators with spiral delivery conduits were used. FIG. 10 shows the release rate per day out to 110 days at 37° C. The release rate data indicate that the systems deliver IFN-ω near the target rate of 22 μg/day through at least day 95 at 37° C.

Example 12

Figure 11:
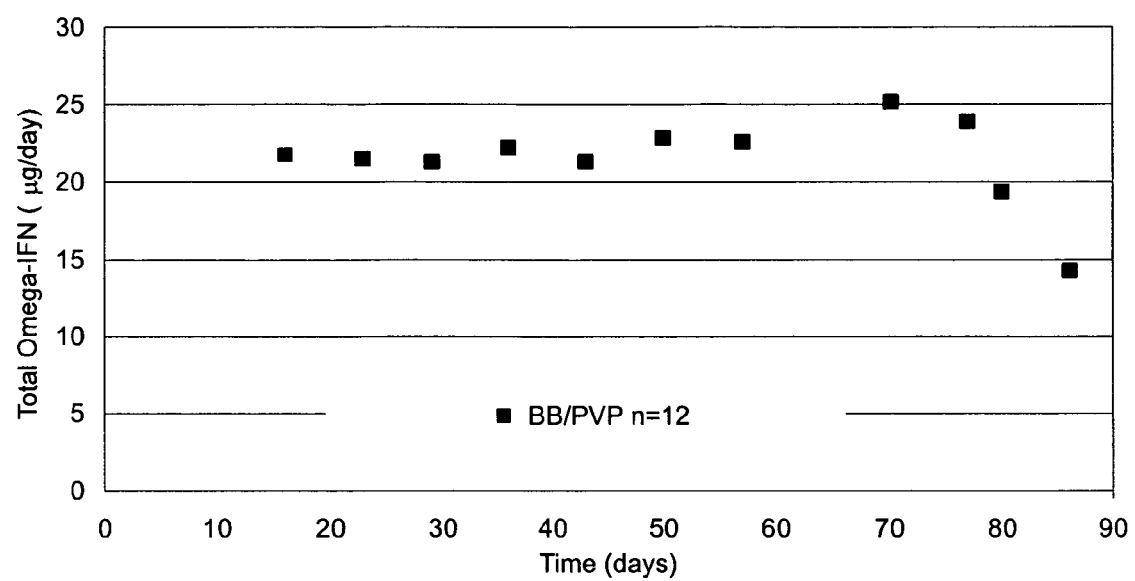
FIG. 11 shows release rate for IFN-ω particle formulation suspended in BB/PVP from osmotic pumps.

Drug reservoirs of several osmotic pumps were filled with approximately 150 μL of suspension formulation as prepared in EXAMPLE 5, i.e., IFN-ω particle formulation (IFN-ω: sucrose:methionine:citrate in a ratio of 1:2:1:2.15) suspended in BB/PVP. Diffusion moderators with spiral delivery conduits were used. The target dose in this example was 25 μg/day. FIG. 11 shows the release rate per day out to 90 days at 37° C. The results indicate that the systems deliver IFN-ω near the target rate through day 90.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An implantable device comprising:
a reservoir containing a suspension formulation comprising
a non-aqueous, single-phase vehicle consisting essentially of about 20% to 60% (w/w) benzyl benzoate and about 40% to 80% (w/w) polyvinylpyrrolidone, the vehicle exhibiting viscous fluid characteristics; and
a particle formulation dispersed in the vehicle, the particle formulation comprising an interferon, a carbohydrate, methionine, and a buffer.

2. The implantable device of claim 1, wherein the reservoir contains 0.5 to 2.5 mg of the interferon.

3. The implantable device of claim 1, the device capable of providing continuous delivery of the interferon at a therapeutically effective rate within 1 ug/day to 100 ug/day.

4. The implantable device of claim 1, the device capable of providing continuous delivery of the interferon at a therapeutically effective rate within 10 ug/day to 50 ug/day.

5. The implantable device of claim 1, wherein the polyvinylpyrrolidone has a molecular weight of between about 2,000 to about 1,000,000.

6. The implantable device of claim 1, wherein a concentration of the buffer in the particle formulation is in a range from 5 mM to 50 mM.

7. The implantable device of claim 1, wherein the interferon is interferon omega.

8. The implantable device of claim 1, wherein the carbohydrate is sucrose and the buffer is citrate.

9. The implantable device of claim 1, wherein the vehicle is present in the suspension formulation in an amount greater than 60 wt %.

10. The implantable device of claim 1, wherein the particle formulation is present in the suspension formulation in a range from 0.01 to 40 wt %.

11. The implantable device of claim 1, wherein the interferon is present in the particle formulation in an amount ranging from 0.1 to 99.9 wt %.

12. The implantable device of claim 1, wherein the carbohydrate, methionine, and buffer are each stabilizers and a weight ratio of each stabilizer to the interferon is in a range from 0.1 to 99.9.

13. The implantable device of claim 12, wherein the carbohydrate, methionine, and buffer are each stabilizers and a weight ratio of each stabilizer to the interferon is greater than 0.5.

14. The implantable device of claim 1, wherein the interferon is selected from the group consisting of Type I and Type II interferons.

15. The implantable device of claim 1, wherein the suspension particle formulation comprises 1:2:1:1.5-2.5 interferon:carbohydrate:antioxidant and/or amino acid:buffer.

16. The implantable device of claim 15, wherein the interferon is interferon omega, the carbohydrate is sucrose, the antioxidant and/or amino acid is methionine, and the buffer is citrate.

17. The implantable device of claim 1, wherein the particle formulation is spray dried.

18. The implantable device of claim 1, wherein the particle formulation is lyophilized.

19. The implantable device of claim 1, further comprising an osmotic pump and a delivery orifice.

20. The implantable device of claim 19, wherein particles of the particle formulation are sized for delivery through the delivery orifice.

21. The implantable device of claim 20, wherein the particles have an average particle diameter less than 50 um.

22. The implantable device of claim 20, wherein the particles have an average particle diameter less than 10 um.

23. The implantable device of claim 20, wherein the particles have an average particle diameter less than 7 um.

24. A method of treating an interferon-responsive disorder comprising implanting in a subject the device of claim 1.

25. The method of claim 24, wherein the disorder is hepatitis C virus disorder.

26. A method of treating an interferon-responsive disorder comprising implanting in a subject the device of claim 16.

27. The method of claim 26, wherein the disorder is hepatitis C virus disorder.

28. The implantable device of claim 1, the device capable of providing continuous delivery of the interferon at a therapeutically effective rate within about 1 ng/day to about 600 ug/day.

29. An implantable device comprising:
a reservoir containing a flowable suspension formulation comprising
a non-aqueous, single-phase vehicle consisting essentially of about 20% to 60% (w/w) benzyl benzoate and about 40% to 80% (w/w) polyvinylpyrrolidone, the vehicle exhibiting viscous fluid characteristics; and
a particle formulation dispersed in the vehicle, the particle formulation comprising an interferon, a carbohydrate, methionine, and a buffer, wherein the device comprises an osmotic pump and is capable of delivering the flowable suspension formulation at a uniform, controlled rate over at least about 1 month.

30. An implantable device comprising:
a reservoir containing a flowable suspension formulation comprising a non-aqueous, single-phase vehicle consisting essentially of about 20% to 60% (w/w) benzyl benzoate and about 40% to 80% (w/w) polyvinylpyrrolidone, the vehicle exhibiting viscous fluid characteristics; and
a particle formulation dispersed in the vehicle, the particle formulation comprising an interferon, a carbohydrate, methionine and a buffer, wherein the particle formulation has a moisture content of about 5% or below by weight.

31. The implantable device of claim 1, wherein the non-aqueous, single-phase vehicle consists essentially of about 50% (w/w) polyvinylpyrrolidone and about 50% (w/w) benzyl benzoate.

32. The implantable device of claim 1, wherein the carbohydrate of the particle formulation is selected from the group consisting of monosaccharides, disaccharides, and alditols.

33. The implantable device of claim 1, wherein the interferon of the particle formulation is selected from the group consisting of interferon alpha, interferon beta, interferon gamma, and interferon omega.

* * * * *

UNITED STATES PATENT AND TRADEMARK OFFICE
CERTIFICATE OF CORRECTION

| | | |
|---|---|---|
| PATENT NO. | : 7,655,254 B2 | Page 1 of 1 |
| APPLICATION NO. | : 11/347601 | |
| DATED | : February 2, 2010 | |
| INVENTOR(S) | : Paula Dennis et al. | |

It is certified that error appears in the above-identified patent and that said Letters Patent is hereby corrected as shown below:

Title page, item (75) inventors: Delete "San Francisco", insert --Milpitas--.

Column 17, line 50-51, claim 15: Delete "suspension".

Signed and Sealed this

Thirtieth Day of March, 2010

David J. Kappos
*Director of the United States Patent and Trademark Office*